United States Patent
Puusaari et al.

(10) Patent No.: US 7,409,037 B2
(45) Date of Patent: Aug. 5, 2008

(54) X-RAY FLUORESCENCE ANALYZER HAVING MEANS FOR PRODUCING LOWERED PRESSURE, AND AN X-RAY FLUORESCENCE MEASUREMENT METHOD USING LOWERED PRESSURE

(75) Inventors: Erkki Tapani Puusaari, Espoo (FI); Hannu Rintamäki, Espoo (FI)

(73) Assignee: Oxford Instruments Analytical Oy (FI)

( * ) Notice: Subject to any disclaimer, the term of this patent is extended or adjusted under 35 U.S.C. 154(b) by 0 days.

(21) Appl. No.: 11/429,172

(22) Filed: May 5, 2006

(65) Prior Publication Data

US 2007/0269003 A1     Nov. 22, 2007

(51) Int. Cl.
    G01N 23/223 (2006.01)
(52) U.S. Cl. .................................. 378/44; 378/45
(58) Field of Classification Search ............ 378/44–50; 250/461.1
    See application file for complete search history.

(56) References Cited

U.S. PATENT DOCUMENTS 5,170,418 A * 12/1992 Ebinuma ..................... 378/34
5,407,641 A * 4/1995 Katschnig et al. ............ 422/107
6,909,770 B2   6/2005 Schramm et al.
6,922,455 B2 * 7/2005 Jurczyk et al. ................ 376/144
7,072,439 B2 * 7/2006 Radley et al. ................. 378/47

FOREIGN PATENT DOCUMENTS

JP     62-280645 A   * 12/1987

* cited by examiner

*Primary Examiner*—Jurie Yun
(74) *Attorney, Agent, or Firm*—Wood, Phillips, Katz, Clark & Mortimer

(57) ABSTRACT

An X-ray fluorescence analyzer has a structure that defines a chamber (102). There is a window (103) to the chamber in a surface that is to come next to a sample (101) outside the chamber. The window (103) comprises a foil that is permeable to X-rays. A detector (104) receives fluorescent X-rays through said window (103). A low pressure source (508) is coupled to the chamber (102) and configured to controllably lower the pressure of a gaseous medium in the chamber (102) to a pressure value between 760 torr and 10 torr. The X-ray fluorescence analyzer maintains a lowered pressure of a value between 760 torr and 10 torr in the chamber (102) for the duration of an X-ray fluorescence measurement.

11 Claims, 4 Drawing Sheets

X-RAY FLUORESCENCE ANALYZER HAVING MEANS FOR PRODUCING LOWERED PRESSURE, AND AN X-RAY FLUORESCENCE MEASUREMENT METHOD USING LOWERED PRESSURE

TECHNICAL FIELD

The invention relates in general to the technology of X-ray fluorescence (XRF) analyzer devices. In particular the invention concerns the technology of enhancing measurements of X-ray fluorescence peaks at low energies in the order of only few kiloelectronvolts.

BACKGROUND OF THE INVENTION

X-ray fluorescence is a measurement and analysis method in which incident X-rays coming from an X-ray source are allowed to hit a sample, causing electrons in the inner shells of constituent atoms to achieve excited states. When these excited states relax, the sample material emits fluorescent radiation at characteristic energies. Measuring the intensity and spectral characteristics of the fluorescent radiation with a detector allows deducing various facts about the material composition of the sample.

X-ray fluorescence analysis is commonly used for scrap sorting and other needs of metal industry, to quickly identify the composition of alloys. Problems may arise with light element constituents such as Mg, Si, Al, and others, because some of the characteristic X-ray fluorescence radiation of these elements comes at energies of only few keV (kiloelectronvolts). For example the K alpha line of Mg at 1.25 keV experiences heavy attenuation in air, so that in an analyzer device with an air gap of 0.9 cm between the sample and the detector something like 88% of the Mg-K radiation is attenuated before reaching the detector.

A prior art publication U.S. Pat. No. 6,909,770 B2 (Schramm et al.) discloses an X-ray fluorescence analyzer equipped with a chamber at the front part of the device, where the X-ray source and detector are located. The front wall of the chamber defines an opening, with a sealing mechanism around its edge. The sealing is pressed against a solid sample surface, which closes the chamber. A separate pump attached to the analyzer device draws all air out of the chamber. As examples of achieved conditions the document mentions a pressure range of 1 to 10-7 torr, or a more narrowly defined range of 1 to 10-2 torr. This reduces significantly the attenuation of X-rays in the free space between the sample and the detector, so said prior art device achieves a remarkable improvement in measuring fluorescent radiation at low energies.

A disadvantage of the prior art device is the additional clumsiness that the external pump arrangement introduces. The pump arrangement also draws a significant amount of electric energy, so that it needs a direct connection to an electric wall outlet. Therefore the apparatus is not well suited for field conditions. Additionally the apparatus is only applicable for analysing samples that have a smooth, solid outer surface, because otherwise it is impossible to seal the front end of the chamber tightly against the sample.

SUMMARY OF THE INVENTION

An objective of the present invention is to provide a compact and efficient XRF analyzer device that is capable of measuring light elements also in field conditions. Another objective of the present invention is to provide an XRF measurement method applicable to measuring light elements easily and efficiently.

The objectives of the invention are achieved by providing the analyzer apparatus with an integrated air pump, which is capable of significantly lowering the pressure in an airtight chamber located at the front end of the analyzer apparatus.

An X-ray fluorescence analyzer according to the invention is characterized in that it comprises:
- a structure that defines a chamber;
- a window to the chamber in a surface configured to come next to a sample that is on the outside of the chamber, said window comprising a foil that is permeable to X-rays;
- a detector configured to receive fluorescent X-rays through said window; and
- a low pressure source coupled to the chamber and configured to controllably lower the pressure of a gaseous medium in the chamber to a pressure value between 760 torr and 10 torr;
- wherein the X-ray fluorescence analyzer is configured to maintain a lowered pressure of a value between 760 torr and 10 torr in the chamber for the duration of an X-ray fluorescence measurement.

A very large pressure difference between a closed chamber emptied of air and its environment requires all wall structures of the chamber to be relatively thick in order to withstand the pressure that tries to crush the chamber. Thus, if one tried to replace the open-faced front end chamber disclosed in U.S. Pat. No. 6,909,770 with a closed chamber, in which a solid front window would offer an entrance to X-rays, the window should be so thick in order to achieve the required mechanical strength that it would cause much more attenuation to soft X-rays than what would be saved by pumping air out of the chamber.

However, it has been found that even a relatively modest reduction in air pressure causes a significant increase in transmittivity to X-rays. Surprisingly, it appears to be possible to find an optimum range of internal pressure for a closed chamber, so that the reduced attenuation in air outweighs the additional attenuation introduced by an entrance window that is needed to close the chamber. What is more, said optimum range of internal pressure is possible to achieve with a relatively small pump that only needs a small amount of energy to operate. This enables integrating the pump with even a hand-held XRF analyzer apparatus.

According to one aspect of the present invention there is provided an X-ray fluorescence analyzer, one part of which is designed to come into close contact with a sample. This part of the analyzer apparatus is equipped with a controllable X-ray source and a radiation detector configured to detect fluorescent X-rays induced in the sample upon bombardment with incident X-rays from the X-ray source. Said part of the analyzer apparatus also comprises an essentially airtight chamber, a wall of which comprises a window, which is permeable to X-rays. The geometry of the chamber, the window and the radiation detector allows fluorescent X-rays from a sample outside the window to pass through the window and across a part of the chamber to hit the detector.

A conduit leads from said chamber to a low pressure source, which is most advantageously a pump, although also other kinds of low pressure sources can be used. Using the low pressure source it is possible to controllably lower the pressure inside the chamber to a certain value that is low enough to significantly reduce attenuation of soft X-rays in the gaseous medium that fills the chamber, but still high enough not to cause excessive mechanical stress to the walls of the chamber, particularly the window.

The transmittivity to X-rays of the gaseous medium in the chamber depends strongly on its density. If the original intensity of fluorescent X-rays is to be determined, it is mandatory to have some knowledge about said density. This knowledge is easy to obtain by equipping the chamber with sensors sensing pressure and temperature, and calculating the density of the gaseous medium from the state equation of gases.

The exemplary embodiments of the invention presented in this patent application are not to be interpreted to pose limitations to the applicability of the appended claims. The verb "to comprise" is used in this patent application as an open limitation that does not exclude the existence of also unrecited features. The features recited in depending claims are mutually freely combinable unless otherwise explicitly stated.

The novel features which are considered as characteristic of the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF DRAWINGS

FIG. 1 illustrates schematically a front end of an X-ray fluorescence analyzer. The use of the conventional designation "front" only illustrates the fact that this part of the X-ray fluorescence analyzer will come close to a sample 101, and does not include any directional limitations. The structures of the X-ray fluorescence analyzer define a chamber 102, one limiting surface of which is a window 103 in that surface that is to be brought into the close vicinity of the sample 101. The radiation input of a detector 104 is located inside the chamber 102, so that suitably directed fluorescent radiation from the sample 101 may enter the chamber 102 through the window 103 and hit the detector 104. In this embodiment of the invention also the radiation output of a controllable X-ray source 105 is located inside the chamber 102. Incident radiation from the X-ray source 105 is directed through the window 103 to the sample 101.

We assume first that the chamber 102 contains air under normal atmospheric pressure. As was noted in the description of prior art above, this would result in heavy attenuation of fluorescent radiation in the energy range of only few keV. In order to reduce attenuation in the gaseous substance filling the chamber, there is a conduit 106 that leads to a low pressure source (not shown). An electrically controlled valve 107 can be used to open and close the conduit 106 according to need. Before commencing the X-ray fluorescence measurement, the valve 107 is opened and the low pressure source is allowed to draw air from the chamber 102, so that the pressure inside the chamber assumes a value lower than the atmospheric pressure.

Figure 2:
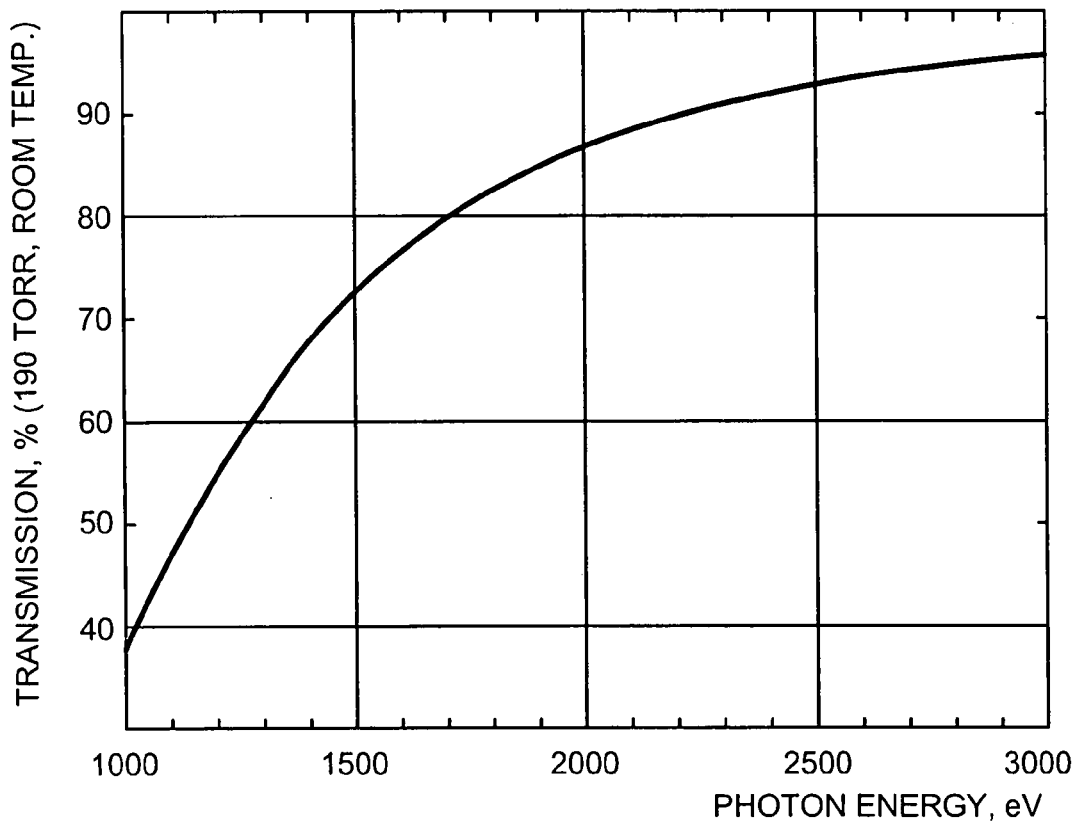
FIG. 2 illustrates attenuation in a 0.9 cm air gap of lowered air pressure as a function of radiation energy.
Figure 3:
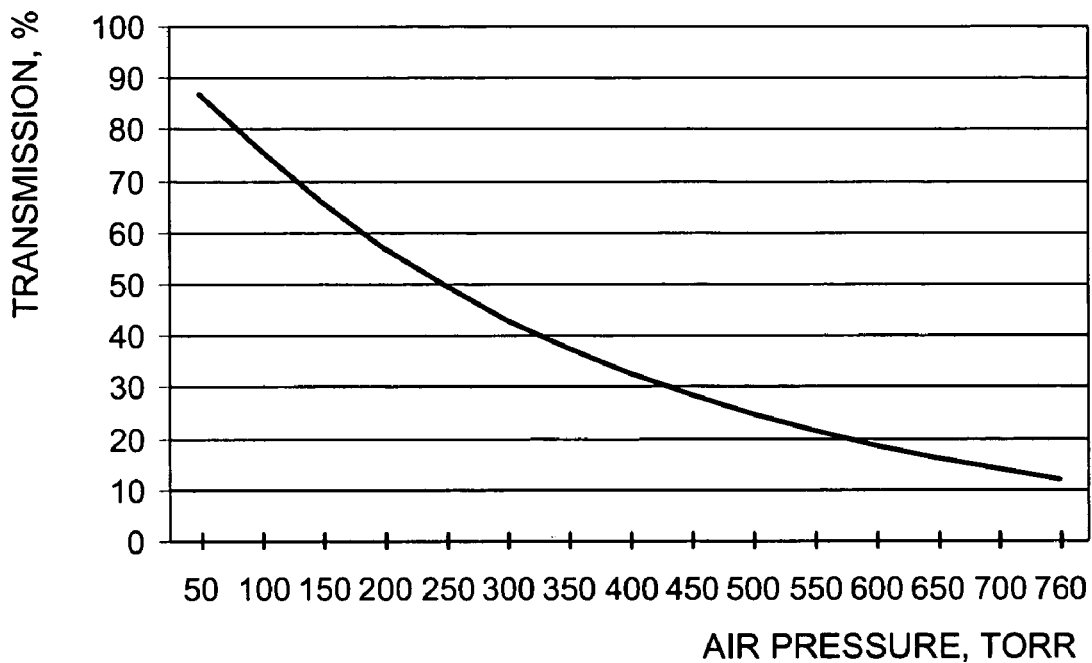
FIG. 3 illustrates attenuation of the K alpha line of Mg in a 0.9 cm air gap as function of air pressure.

Defining an optimum value for the lowered internal pressure of the chamber 102 deserves some consideration. FIG. 2 illustrates how the transmittivity of an air gap of 0.9 cm depends on photon energy, when air pressure is 190 torr and the measurement is made at room temperature. The pressure of 190 torr is one fourth of the nominal atmospheric pressure (760 torr). At higher pressures, the left part of the transmittivity curve drops more steeply, while at lower pressures it slopes more and more gently. Changes are less significant towards the right-hand side of the curve, and at very low pressures the curve naturally begins to resemble a horizontal line at 100%. We can see that at the K alpha energy of Mg, which is approximately 1250 eV, transmittivity at 190 torr is 60% while experiments show that in atmospheric pressure it would be only about 12%. FIG. 3 illustrates how the transmittivity of an 0.9 cm air gap changes for the K alpha energy of Mg as a function of air pressure.

Figure 4:
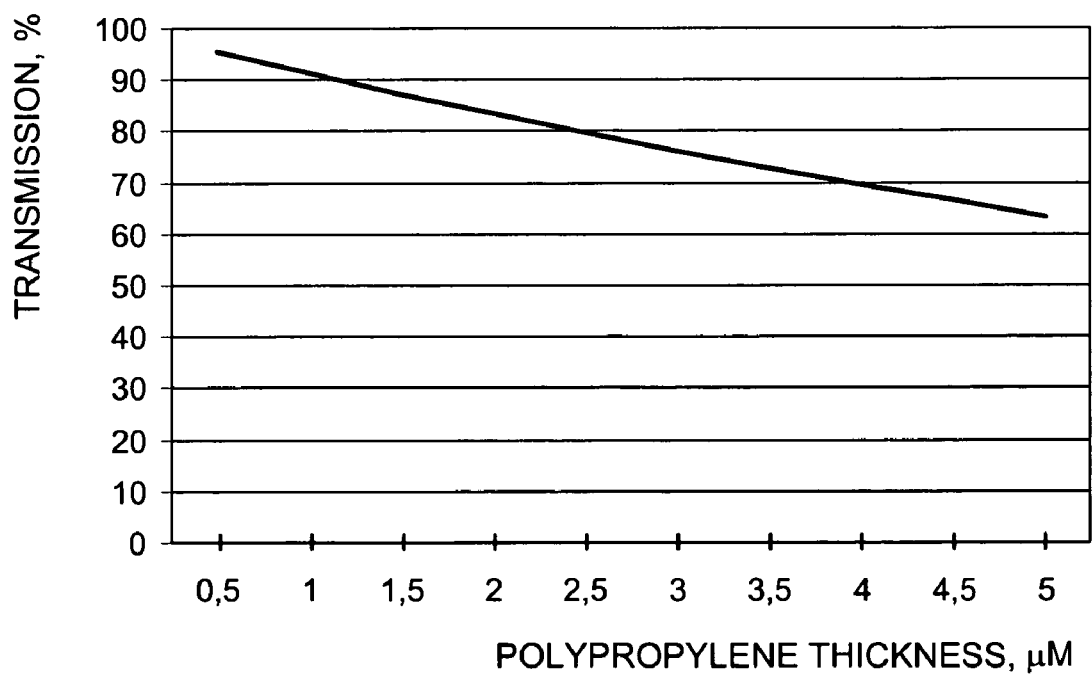
FIG. 4 illustrates attenuation of the K alpha line of Mg in a polypropylene window foil as a function of the foil thickness.

The window 103 is made of a material that is as transparent to X-rays as possible. Good window materials include, but are not limited to, polycarbonate, polypropylene and polyimide, and the thickness of the window foil is typically between 0.5 and 5 micrometers. Said polymer materials exhibit some elasticity, so that when pressure inside the chamber is lowered, the window bulges inwards. Assuming that the sample surface is flat, the bulging of the window creates a bubble-like space between the window and the sample surface. If there is no sealing mechanism at the sample side surface of the X-ray fluorescence analyzer, this bubble-like space is filled with air at atmospheric pressure, creating yet another attenuating layer. It is possible to reduce the amount of bulging by using a thicker window foil, but this may again cause more attenuation. FIG. 4 illustrates the transmittivity of a polypropylene window foil for the K alpha energy of Mg as a function of foil thickness between 0.5 and 5 micrometers. One possibility is to use more advanced window configurations, in which a relatively thin foil is mechanically supported with a support grid that can be either an integral part of the window material or a separate layer next to the actual window foil. Advanced window configurations are known for example from a U.S. patent application Ser. No. 11/281638, which is co-pending and assigned to the same applicant, and incorporated herein in its entirety by reference thereto.

One way to determine an optimum value for the internal pressure of the chamber 102 is to plot the additional attenuation caused by the window foil and the "bulging bubble" as a function of chamber pressure for fluorescent energies in a range of interest, and to select a combination of window structure and internal pressure that together cause the smallest attenuation.

Another aspect to consider in selecting the desired internal pressure value for the chamber is the nature of the low pressure source that should be used to draw air from the chamber. If the analyzer is or comprises a portable, handheld unit, it is very advantageous if the low pressure source is small and light enough to fit inside the device, like a small diaphragm pump for example. Small, lightweight electrically driven pumps typically have certain limitations concerning the maximum pressure difference that they can produce and maintain. For example, a Diaphragm Pump 2003V manufactured by Rietschle Thomas Puchheim GmbH, Germany, has overall dimensions in the order of 20×34×60 mm, draws a maximum current of 350 mA from a DC operating voltage between 4.5 and 9.0 V, weighs only 40 grams and is capable of maintaining a pressure difference of 750 mbar (approximately 570 torr) between its input and output. Other miniature-sized, electrically driven, air-drawing pumps exist too and could be used.

FIG. 3 shows that even a small decrease in chamber pressure already enhances the transmission; for example, decreasing chamber pressure by 30% from 760 torr to about 500 torr will double the transmission from 12% to 24%. Thus, an upper limit for the concept "lowered pressure" in the chamber is only little less than the surrounding atmospheric pressure. A lower limit comes from the performance of the low pressure source used, as well as from the tensile strength of the window material. We believe that it is not practical to aim at lower pressure than approximately 10 torr.

Figure 1:
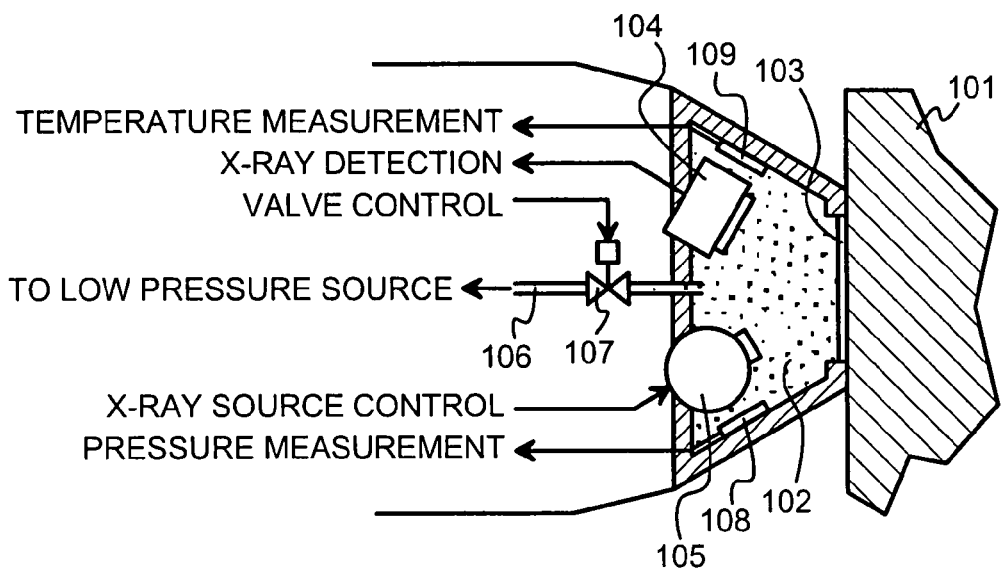
FIG. 1 illustrates a chamber part of an X-ray fluorescence analyzer according to an embodiment of the invention.

It is important to note that prior art solutions, like that of U.S. Pat. No. 6,909,770, suggest drawing essentially all air out of the measurement area (or replacing air with He or other non-attenuating protective gas), to completely exclude attenuation in air. Such an approach means that the measurement does not include, and is not even meant to include, any knowledge about how much attenuation the gaseous medium could have caused; by drawing out all air the attenuation is lowered to a level at which it is not significant any more. According to an aspect of the present invention, using air at lowered pressure is a viable alternative, if the measurement is augmented with accurate additional knowledge about how much attenuation remained. In FIG. 1, there are schematically represented a pressure sensor 108 and a temperature sensor 109 that are configured to give information about the internal pressure and temperature of the chamber 102. From the temperature and pressure information it is straightforward to calculate the density of air inside the chamber using the well-known state equation of gases.

Using pressure and temperature sensors inside the chamber like in FIG. 1 is not the only possible way of detecting the density of air. For example, since in many cases the temperature inside the chamber is essentially the same as the temperature of the chamber walls, it may not be necessary to place a temperature sensor inside the chamber, if one exists close enough to it so that it gives the temperature of the solid structure that defines the chamber. Even pressure can be measured from outside the chamber, for example by using a sensitive strain gauge strip to measure how much some part of the chamber wall deforms under the forces caused by the pressure difference. Yet another possibility to measure the density of air inside the chamber is to let some known part of the radiation produced by the controllable X-ray source to traverse the chamber and hit a detector, so that by comparing the known intensity of incident radiation and the detected amount of radiation across the chamber it is possible to deduce the density of air therebetween.

Figure 5:
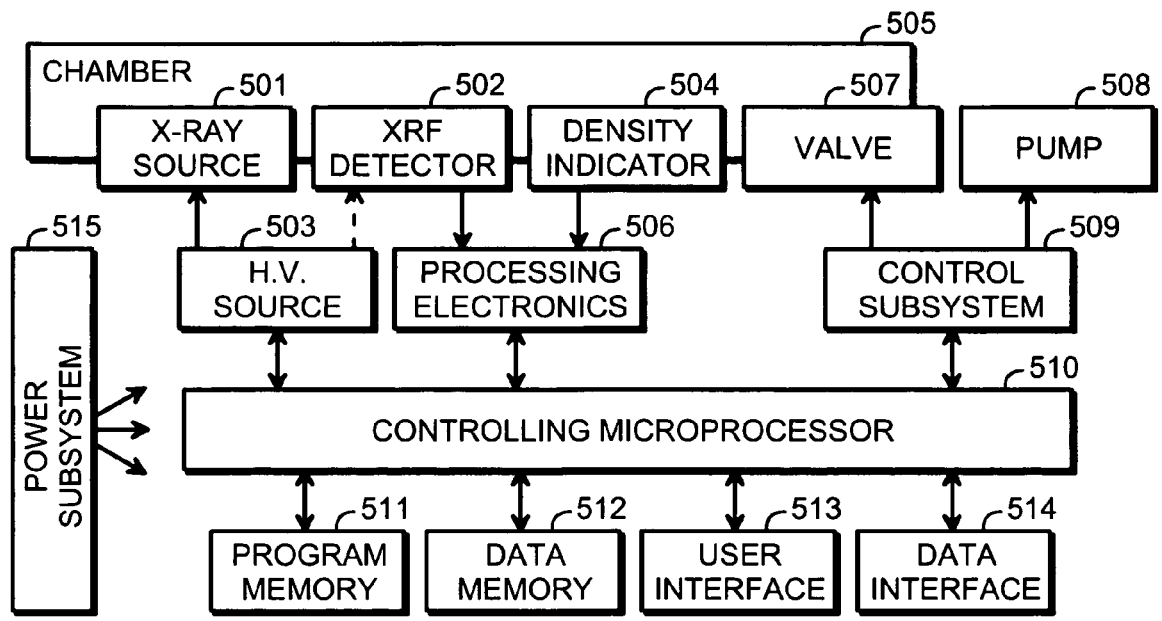
FIG. 5 illustrates a system level approach to an X-ray fluorescence analyzer according to an embodiment of the invention.

FIG. 5 illustrates a system level approach to an XRF analyzer according to an embodiment of the invention. The X-ray source 501 is selected so that the incident X-rays it produces will be useful in exciting the relatively low-energy states of light elements in a sample. The X-ray detector 502 is selected so that it can reliably detect also the relatively low-energy fluorescent radiation coming from such light elements. A high voltage source 503 is coupled to deliver the necessary high voltages at least to the X-ray source 501 and possibly also to the X-ray detector 502, if high voltages are needed there for biasing.

A density indicator subsystem 504 is configured to produce an indication of the density of air inside a chamber 505, through which fluorescent X-rays will go on their way from the sample (not shown) to the X-ray detector 502. As was described above, there are numerous possibilities for implementing the density indicator subsystem 504, one of the most straightforward ways being the use of pressure and temperature sensors. The output signals of the X-ray detector 502 and the density indicator subsystem 504 are coupled to a processing electronics block 506, which is configured to implement signal processing functions such as amplification, pulse shaping, filtering and A/D conversion.

In order to controllably lower the pressure of air in the chamber 505 there is a controllable valve 507 and a low pressure source, here a pump 508, configured to draw air from the chamber 505 through the valve 507. A control subsystem 509 is coupled to the valve 507 and the pump 508 and configured to control their operation (i.e. to open and close the valve 507 and to switch the pump 508 on and off).

A controlling microprocessor 510 is configured to act as the central controlling entity of the XRF analyzer. It controls the operation of the high voltage source 503 and possibly receives feedback therefrom; it receives the measurement information from the processing electronics block 506 and tunes the signal processing operations if needed; and it gives the pressure control commands to the control subsystem 509 and receives feedback. The controlling microprocessor 510 operates by executing a program stored in a program memory 511 and uses a data memory 512 for storing and retrieving data. The controlling microprocessor 510 is also coupled to a user interface 513, which typically comprises keys and/or switches through which a user can give input commands, and a display and/or other sensory indicators, such as lights and buzzers, to give sensory feedback to the user. A data interface 514 is provided and coupled to the controlling microprocessor 510 so that the XRF analyzer may exchange data with other electronic devices. The functionalities that are described here to take place in a single controlling microprocessor 510 may, in a way well known as such, be distributed among a number of different parts or circuits of the XRF analyzer. A conventional power subsystem 515 is configured to feed operating power to all electrically driven parts of the XRF analyzer.

The system level configuration of FIG. 5 is applicable irrespective of whether the XRF analyzer is of a portable, hand-held type or of a benchtop type. In portable devices small size and weight are important design drivers, and power consumption should be minimized because the power subsystem 515 relies on rechargeable batteries for wireless operation. In benchtop devices size and weight are less of a concern, which may allow e.g. the use of more accurately controllable pumps and valves for producing the lowered pressure in the chamber 505.

Figure 6:
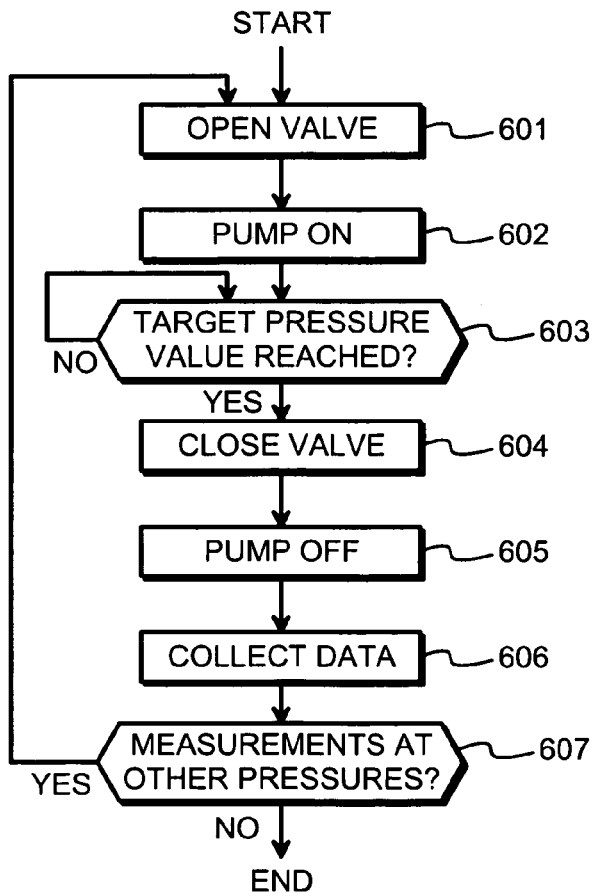
FIG. 6 illustrates certain aspects of a method according to an embodiment of the invention.

FIG. 6 illustrates an exemplary measurement method according to an embodiment of the invention. Here we assume that a complete measurement may, but is not required to, contain multiple partial measurements at different pressures. At step 601 the valve that closes the path between a chamber and a low pressure source is opened and at step 602 the pump that acts as a low pressure source is switched on. Steps 601 and 602 could take place in reverse order or they could be combined, if the pump is of a type that also acts as a valve. Pumping is continued in step 603 until a target pressure value is reached, after which the valve is closed and the pump is switched off at steps 604 and 605 (which could be combined or reversed).

X-ray fluorescence measurement data is collected at step 606. This step thus includes all conventional steps such as irradiating the sample, detecting fluorescent X-rays and processing the detected signal. Basically it would be possible to measure simultaneously while the pump is on, but it is probable that the electric motor of the pump will produce interference signals, which might weaken the measurement accuracy. The pump will also vibrate when operating, which is another possible source of unwanted interference to the X-ray fluorescence measurement. Step 607 represents a check, whether other partial measurements remain to be made at different pressures. A positive finding at step 607 leads to step 601, while a negative finding ends the measurement process.

It may be worthwhile to intermittently or continuously store the readings of the density indicator subsystem during the time period of collecting the X-ray fluorescence data, for example in case a small leak in the system causes the pressure to change or a heat source acting upon the chamber causes the temperature to change. If pressure or temperature changes during the measurement, causing the air density and consequently the absorption in air to vary accordingly, it is possible to either use a mean air density value in the processing of the measurement spectrum, or even to use some more sophisticated algorithms that spread the effect of the changing air density more accurately over the whole duration of the measurement.

Figure 7:
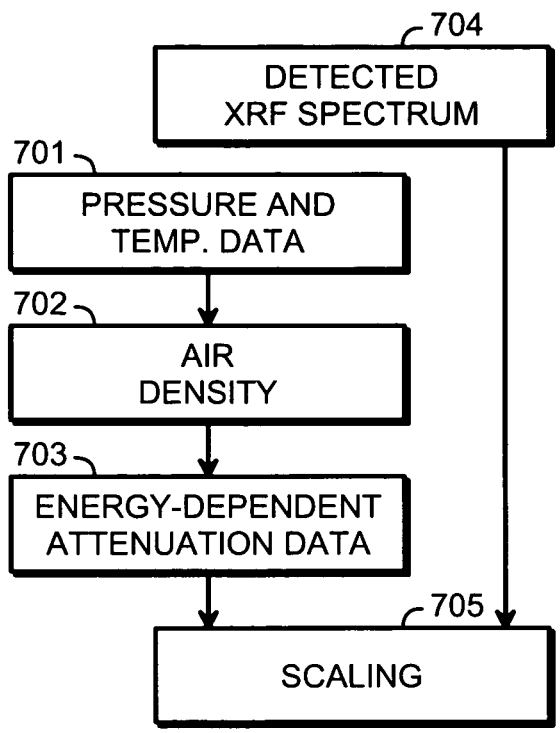
FIG. 7 illustrates some other aspects of a method according to an embodiment of the invention.

FIG. 7 illustrates how a process of analysing the X-ray fluorescence measurement data, collected in a method that involves using lowered air pressure between the sample and the detector, preferably includes the steps necessary to derive the air density 702 from the output data 701 of the density indicator subsystem, to map the derived air density to a characteristic attenuation 703 at each measured fluorescent energy range, and to scale the measured fluorescent spectrum 704 accordingly at step 705 to remove the energy-dependent effect of attenuation in air. It is relatively straightforward to accomplish the scaling steps by storing into memory a mathematical formula that links a given air density value to the corresponding transmission percentage at each energy, or by storing into memory an appropriate number of previously calculated energy- and density-dependent transmission percentage values in the form of look-up tables.

A principle of normalizing certain measured intensity values can be applied in order to reduce the uncertainty caused by attenuation in air. As air that is causing attenuation we may consider the lowered-pressure air that is left in the chamber, and/or the air that will remain between the sample and the input window. The last-mentioned is the more difficult to control otherwise, because it may result from effects that are difficult to anticipate, such as the sample surface being uneven or the formation of the bubble-like air-filled space when the window bulges inwards.

The K alpha lines of light elements like Mg, Si and Al are so close to each other that a layer of air with unknown density and/or layer thickness will cause essentially an identical percentage of attenuation to all of them. Thus, if there were initial radiation intensities A, B, and C for the K alpha lines of Mg, Si, and Al respectively, and an unknown layer of air causes an attenuation of p percent, a detector will detect intensities (100-p)A, (100-p)B, and (100-p)C, respectively. Instead of using for example the detected K alpha intensity (100-p)A for Mg, it is advisable to normalize it by dividing it by an expression that has the unknown transmittivity (100-p) as a common factor. One such expression is the sum of said three detected intensities, so that as an processed intensity value for Mg one would use the ratio A/(A+B+C), from which ratio the common factor (100-p) has been cancelled out.

Figure 8:
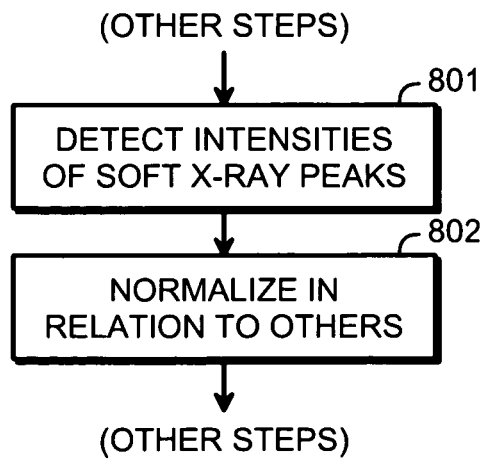
FIG. 8 illustrates method steps for normalizing detected intensity values according to an embodiment of the invention.

It is only advisable to take such detected intensities to the denominator that are close enough to each other so that the unknown attenuation percentage p can reasonably be assumed to be the same for them all. FIG. 8 represents schematically steps of a data processing method in which the acquisition of detected intensity values at step 801 is followed by normalization at step 802.

The exemplary embodiments described above should not be construed to limit the applicability of the invention. For example, at least theoretically it would be possible to use a cryogenic cooling unit as a low pressure source, so that instead of (or in addition to) drawing air from the inside of the chamber to the outside, some part(s) of the walls of the chamber would be cooled enough to cause some of the component gases to solidify onto the cooled spot. However, at least with technology known at the time of writing, pumping air from the chamber is much simpler to do in practice.

We claim:

1. An X-ray fluorescence analyzer, comprising:
   a structure that defines a chamber;
   a window to the chamber in a surface configured to come next to a sample that is on the outside of the chamber, said window comprising a foil that is permeable to X-rays;
   a detector configured to receive fluorescent X-rays through said window;
   a low pressure source coupled to the chamber and configured to controllably lower the pressure of a gaseous medium in the chamber to a pressure value between 760 torr and 10 torr; and
   a density indicator subsystem configured to produce an indication of the density of gaseous medium inside the chamber;
   wherein the X-ray fluorescence analyzer is configured to maintain a lowered pressure of a value between 760 torr and 10 torr in the chamber for the duration of an X-ray fluorescence measurement.

2. An X-ray fluorescence analyzer according to claim 1, wherein the density indicator subsystem comprises a pressure sensor configured to sense the pressure of the gaseous medium inside the chamber.

3. An X-ray fluorescence analyzer according to claim 1, wherein the density indicator subsystem comprises a temperature sensor configured to sense the temperature of the gaseous medium inside the chamber.

4. An X-ray fluorescence analyzer according to claim 3, wherein the temperature sensor is outside the chamber, so that it is configured to only indirectly sense the temperature of the gaseous medium inside the chamber by sensing the temperature of the structure that defines the chamber.

5. An X-ray fluorescence analyzer according to claim 1, wherein the low pressure source is a pump integrated to the X-ray fluorescence analyzer.

6. An X-ray fluorescence analyzer according to claim 5, comprising:
   a conduit configured to lead gaseous medium from the chamber to said pump; and
   an electrically controllable valve along said conduit.

7. A method for making an X-ray fluorescence measurement of a sample, comprising:
   drawing gaseous medium from a chamber, a part of which is located between the sample and a detector, until the pressure of gaseous medium inside said chamber is at a predefined value between 760 torr and 10 torr;
   maintaining the pressure of said gaseous medium at said predefined value;
   receiving fluorescent X-rays from said sample to said detector through a window that constitutes a part of a structure defining said chamber while maintaining the pressure of said gaseous medium at said predefined value;

detecting and storing the intensity at certain energies of the received fluorescent X-rays; and obtaining an indication of the density of gaseous medium inside said chamber during the reception of fluorescent X-rays.

8. A method according to claim 7, wherein obtaining an indication of the density of gaseous medium inside said chamber comprises obtaining an indication of at least one of pressure and temperature inside said chamber.

9. A method according to claim 8, comprising deriving the density of gaseous medium inside said chamber through applying the state equation of gases.

10. A method according to claim 7, comprising signal processing in which an effect of attenuation in gaseous medium is compensated for in the stored fluorescent X-ray intensities through using knowledge about the density of gaseous medium in the chamber during the reception of fluorescent X-rays.

11. A computer-readable medium encoded with a data structure, comprising machine-readable instructions that when executed on a computer cause the execution of the steps of:

allowing a low pressure source to draw gaseous medium from a chamber, a part of which is located between a sample and a detector, until the pressure of gaseous medium inside said chamber is at a predefined value between 760 torr and 10 torr;

maintaining the pressure of said gaseous medium at said predefined value;

receiving fluorescent X-rays from said sample to said detector through a window that constitutes a part of a structure defining said chamber while maintaining the pressure of said gaseous medium at said predefined value;

detecting and storing the intensity at certain energies of the received fluorescent X-rays; and compensating for an effect of attenuation in gaseous medium in the stored fluorescent X-ray intensities through using knowledge about the density of gaseous medium in the chamber during the reception of fluorescent X-rays.

* * * * *